(12) United States Patent
Naik et al.

(10) Patent No.: US 9,630,175 B2
(45) Date of Patent: Apr. 25, 2017

(54) SELF-ALIGNED NANOGAP FABRICATION

(71) Applicant: INTEL CORPORATION, Santa Clara, CA (US)

(72) Inventors: Nisarga Naik, Santa Clara, CA (US); Oguz H. Elibol, Sunnyvale, CA (US)

(73) Assignee: INTEL CORPORATION, Santa Clara, CA (US)

(*) Notice: Subject to any disclaimer, the term of this patent is extended or adjusted under 35 U.S.C. 154(b) by 28 days.

(21) Appl. No.: 14/583,368

(22) Filed: Dec. 26, 2014

(65) Prior Publication Data

US 2016/0184819 A1   Jun. 30, 2016

(51) Int. Cl.
*H01B 13/00* (2006.01)
*B01L 3/00* (2006.01)
*C23C 16/56* (2006.01)

(52) U.S. Cl.
CPC ... *B01L 3/502707* (2013.01); *B01L 3/502715* (2013.01); *C23C 16/56* (2013.01); *B01L 2200/025* (2013.01); *B01L 2200/0663* (2013.01); *B01L 2200/10* (2013.01); *B01L 2200/12* (2013.01); *B01L 2300/0645* (2013.01); *B01L 2300/0816* (2013.01);
(Continued)

(58) Field of Classification Search
CPC ........ B01L 3/50; B01L 3/5023; B01L 3/5027; B01L 2200/0663; B01L 2200/10; B01L 2200/12; B01L 2300/0838; B01L 2300/0645; B01L 2300/0896; H01L 21/768; H01L 21/76804; H01L 21/76805
USPC ......... 216/13, 17, 18, 39; 438/259, 672, 700
See application file for complete search history.

(56) References Cited

U.S. PATENT DOCUMENTS

| | | |
|---|---|---|
| 6,824,974 B2 | 11/2004 | Pisharody et al. |
| 8,372,585 B2 | 2/2013 | Su et al. |
| 8,500,979 B2 | 8/2013 | Elibol et al. |

(Continued)

FOREIGN PATENT DOCUMENTS

| | | |
|---|---|---|
| WO | WO 03/020946 A2 | 3/2003 |
| WO | WO 2006/088425 A1 | 8/2006 |

(Continued)

OTHER PUBLICATIONS

International Search Report issued Apr. 8, 2016 in corresponding International Patent Application No. PCT/US2015/061491(3 pages).

(Continued)

*Primary Examiner* — Lan Vinh
(74) *Attorney, Agent, or Firm* — Pillsbury Winthrop Shaw Pittman LLP

(57) ABSTRACT

Disclosed herein is a method comprising: depositing a second electrode of each of a plurality of electrode pairs onto a substrate, through an opening of one or more resist layers; depositing a strip of a sacrificial layer directly on the second electrode through the same opening of the one or more resist layer; depositing a first electrode of each of the plurality of electrode pairs directly on the strip of the sacrificial layer through the same opening of the one or more resist layer; and forming a nanogap channel by removing the strip of the sacrificial layer; wherein the strip of the sacrificial layer is sandwiched between and in direct contact with the first electrode and the second electrode before the strip is removed, and wherein at least a portion of the first electrode directly faces at least a portion of the second electrode.

18 Claims, 20 Drawing Sheets

(52) U.S. Cl.
CPC .......... *B01L 2300/0838* (2013.01); *B01L 2300/0887* (2013.01); *B01L 2300/0896* (2013.01); *B01L 2300/163* (2013.01)

(56) References Cited

U.S. PATENT DOCUMENTS

| | | | |
|---|---|---|---|
| 8,563,240 B2 | 10/2013 | Su et al. | |
| 8,674,086 B2 | 3/2014 | Liu et al. | |
| 8,715,932 B2 | 5/2014 | Su et al. | |
| 8,962,279 B2 | 2/2015 | Liu et al. | |
| 8,986,928 B2* | 3/2015 | Turner | C12Q 1/6869 435/6.1 |
| 9,040,237 B2 | 5/2015 | Koo et al. | |
| 2006/0276031 A1* | 12/2006 | Nam | H01L 21/02063 438/633 |
| 2010/0330553 A1 | 12/2010 | Su et al. | |
| 2012/0175694 A1* | 7/2012 | Ho | H01L 21/76264 257/301 |
| 2013/0306473 A1* | 11/2013 | Kaetelhoen | G01N 27/3277 204/403.01 |
| 2014/0001055 A1 | 1/2014 | Elibol et al. | |
| 2014/0190824 A1* | 7/2014 | Credo | B82Y 15/00 204/403.15 |

FOREIGN PATENT DOCUMENTS

| | | |
|---|---|---|
| WO | WO 2013/089742 A1 | 6/2013 |
| WO | WO 2013/100949 A1 | 7/2013 |

OTHER PUBLICATIONS

U.S. Appl. No. 11/073,160, titled "Sensor Arrays and Nucleic Acid Sequencing Applications," filed Mar. 4, 2005.

* cited by examiner

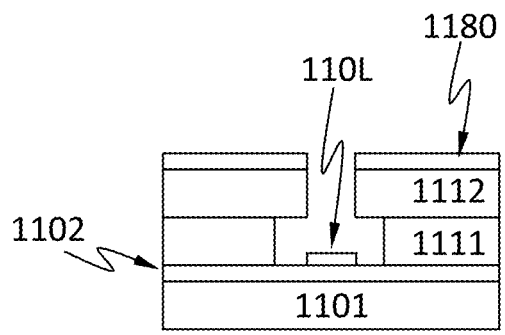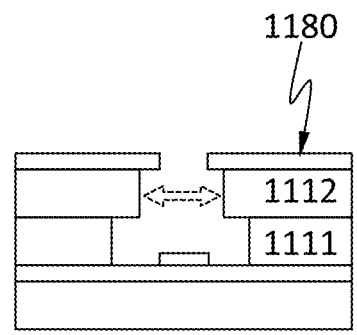
Fig. 11A  Fig. 11B
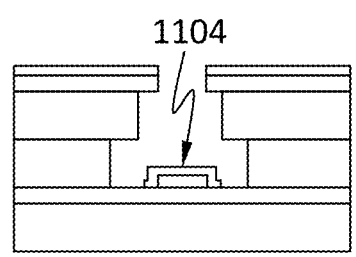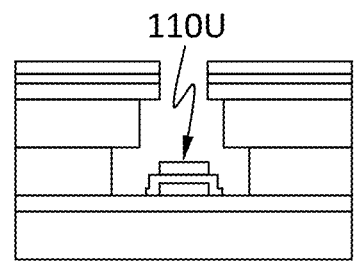
Fig. 11C  Fig. 11D
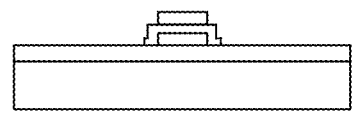
Fig. 11E

SELF-ALIGNED NANOGAP FABRICATION

This invention was made with Government support under contract number 7R01HG006882-02 awarded by the National Institutes of Health. The Government has certain rights in this invention.

CROSS-REFERENCE TO RELATED APPLICATIONS

Reference is made to commonly owned and co-pending U.S. application Ser. No. 12/655,578 titled "Nanogap Chemical and Biochemical Sensors," filed Dec. 31, 2009, now pending; U.S. patent application Ser. No. 11/226,696, titled "Sensor Arrays and Nucleic Acid Sequencing Applications," filed Sep. 13, 2005, now pending; which is a continuation-in-part application that claims the benefit of U.S. patent application Ser. No. 11/073,160, titled "Sensor Arrays and Nucleic Acid Sequencing Applications," filed Mar. 4, 2005; U.S. patent application Ser. No. 11/967,600, titled "Electronic Sensing for Nucleic Acid Sequencing," filed Dec. 31, 2007 now pending; U.S. patent application Ser. No. 12/319,168, titled "Nucleic Acid Sequencing and Electronic Detection," filed Dec. 31, 2008, now pending; U.S. patent application Ser. No. 12/459,309, titled "Chemically Induced Optical Signals and DNA Sequencing," filed Jun. 30, 2009, now pending; U.S. patent application Ser. No. 12/655,459, titled "Solid-Phase Chelators and Electronic Biosensors," filed Dec. 30, 2009, now pending; U.S. patent application Ser. No. 12/823,995, titled "Nucleotides and Oligonucleotides for Nucleic Acid Sequencing," filed Jun. 25, 2010, now pending; U.S. patent application Ser. No. 12/860,462, titled "Nucleic Acid Sequencing," filed Aug. 20, 2010, now pending; International Patent Application PCT/US2011/067520, titled "Nanogap Transducers with Selective Surface Immobilization Sites," filed Dec. 28, 2011; International Patent Application PCT/US2011/065154, titled "Diamond Electrode Nanogap Transducers," filed Dec. 15, 2011; and U.S. patent application Ser. No. 13/538,346, titled "High throughput biochemical detection using single molecule fingerprinting arrays," filed on Jun. 29, 2012; the disclosures of which are incorporated herein by reference. Appropriate components for device/system/method/process aspects of the each of the foregoing patents and patent publications may be selected for the present disclosure in embodiments thereof.

TECHNICAL FIELD

The present disclosure relates to a method and a device suitable for single molecule detection and especially suitable for single molecule sequencing of molecules such as DNA, RNA, and peptides.

BACKGROUND

Single-molecule sequencing enables molecules such as DNA, RNA, and peptides to be sequenced directly from biological samples without steps such as purification, separation, amplification of the molecules themselves. Single-molecule sequencing is thus well-suited for diagnostic and clinical applications.

The classical DNA sequencing technology (sometimes referred to as first generation sequencing technology) was developed in the late 1970s and evolved from a low-throughput approach, in which the same radiolabeled DNA sample was run on a gel with one lane for each nucleotide, to an automated method in which all four fluorescently labeled dye terminators for a single sample were loaded onto individual capillaries. These capillary-based instruments could handle hundreds of individual samples per week and were used in obtaining the first draft sequence of a human genome. Various improvements in components used in this technology pushed read lengths up to 1,000 base pairs (bp) without much improvement on the underlying principle.

The second generation sequencing technology emerged in 2005 and increases the throughput by at least two orders of magnitude over the first generation sequencing technology. Representative platforms include pyrosequencing (454 Life Sciences), Solexa (Illumina) and SOLiD (Applied Biosystems). The second generation sequencing technology is superior to its predecessor because the sequencing target changed from single clones or samples to many independent DNA fragments, enabling large sets of DNAs to be sequenced in parallel. Many platforms in this generation achieved massively parallel sequencing by imaging light emission from the sequenced DNA, or by detecting hydrogen ions (Ion Torrent by Life Technologies). The second generation sequencing technology avoids the bottleneck that resulted from the individual preparation of DNA templates required in the first generation technology. Read lengths of the second generation sequencing technology have exceeded 400 bp at an error rate below 1%.

The second generation sequencing technology still requires amplification of template. Amplification may cause quantitative and qualitative artifacts that can have detrimental impacts on quantitative applications, such as chromatin immunoprecipitation sequencing (ChIP-Seq) and RNA/cDNA sequencing. Amplification also places limitations on the size of the template being sequenced because molecules that are too short or too long tend not to be amplified well.

The third generation sequencing technology allows sequencing one or a few copies of a molecule and thus is often referred to as the single-molecule sequencing technology. The third generation sequencing technology thus simplifies sample preparation, reduces sample mass requirements, and most importantly eliminates amplification of templates. The third generation sequencing technology tends to have high read lengths, low error rates and high throughput. The third generation sequencing technology allows resequencing the same molecule multiple times for improved accuracy and sequencing molecules that cannot be readily amplified, for example because of extremes of guanine-cytosine content, secondary structure, or other reasons. These characteristics of the third generation sequencing technology make it well suited for diagnostic and clinical applications.

The third generation sequencing technology encompasses a wide variety of platforms that differ in their fundamental principles. Representative platforms include sequencing by synthesis, optical sequencing and mapping, and nanopores.

Sequencing by Synthesis

One representative sequencing-by-synthesis platform involves hybridizing individual molecules to a flow cell surface containing covalently attached oligonucleotides, sequentially adding fluorescently labeled nucleotides and a DNA polymerase, detecting incorporation events by laser excitation, and recording with a charge coupled device (CCD) camera. The fluorescent nucleotide prevents the incorporation of any subsequent nucleotide until the nucleotide dye moiety is cleaved. The images from each cycle are assembled to generate an overall set of sequence reads.

Another representative sequencing-by-synthesis platform involves constraining DNA to a zero-mode wave guide so small that light can penetrate only the region very close to the edge of the wave guide, where the polymerase used for sequencing is constrained. Only nucleotides in that small volume near the polymerase can be illuminated and their fluorescence can be detected. All four potential nucleotides are included in the reaction, each labeled with a different color fluorescent dye so that they can be distinguished from each other.

Yet another representative sequencing-by-synthesis platform is based on the fluorescence resonance energy transfer (FRET). This platform uses a quantum-dot-labeled polymerase that synthesizes DNA and four distinctly labeled nucleotides in a real-time system. Quantum dots, which are fluorescent semiconducting nanoparticles, have an advantage over fluorescent dyes in that they are much brighter and less susceptible to bleaching, although they are also much larger and more susceptible to blinking. The sample to be sequenced is ligated to a surface-attached oligonucleotide of defined sequence and then read by extension of a primer complementary to the surface oligonucleotide. When a fluorescently labeled nucleotide binds to the polymerase, it interacts with the quantum dot, causing an alteration in the fluorescence of both the nucleotide and the quantum dot. The quantum dot signal drops, whereas a signal from the dye-labeled phosphate on each nucleotide rises at a characteristic wavelength.

Optical Sequencing and Mapping

Optical sequencing and mapping generally involves immobilizing a DNA molecule to be sequenced to a surface, cutting it with various restriction enzymes or labeling it after treatment with sequence-specific nicking enzymes.

Nanopores

Sequencing by synthesis and optical sequencing and mapping platforms use some kind of label to detect the individual base for sequencing. In contrast, nanopore platforms generally do not require an exogenous label but rely instead on the electronic or chemical structure of the different nucleotides for discrimination. Representative nanopores include those based on solid-state materials such as carbon nanotubes or thin films and those based on biological materials such as α-hemolysin or MspA.

BRIEF DESCRIPTION OF THE DRAWINGS

The above aspects and other aspects and features will become apparent to those ordinarily skilled in the art upon review of the following description of specific embodiments in conjunction with the accompanying figures, wherein:

FIGS. 11A-11E show an exemplary fabrication method for the device in FIGS. 1A-1E, according to an embodiment.

DETAILED DESCRIPTION

Figure 1A:
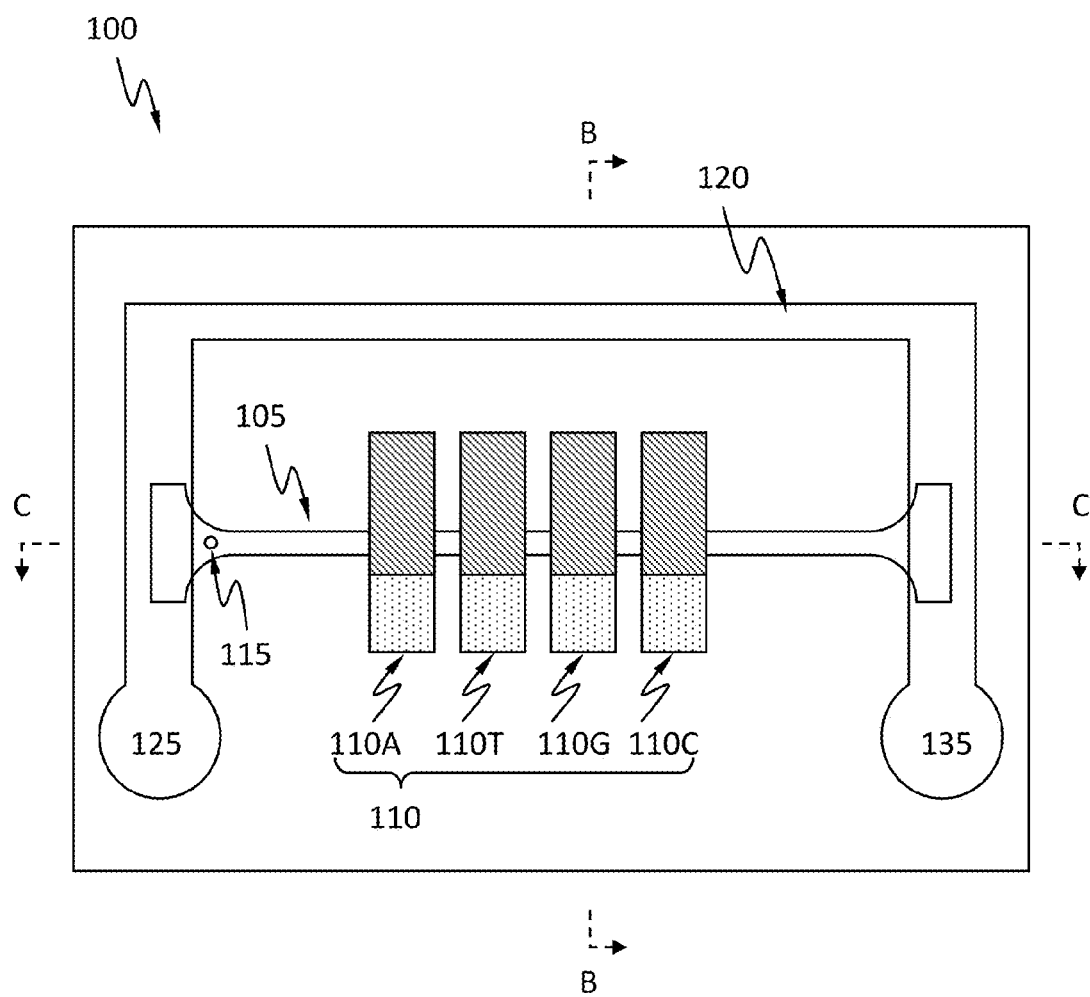
FIG. 1A-FIG. 1E schematically show the structure of a device suitable single molecule sequencing, according to an embodiment.

Embodiments will now be described in detail with reference to the drawings, which are provided as illustrative examples so as to enable those skilled in the art to practice the embodiments. Notably, the figures and examples below are not meant to limit the scope to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the embodiments will be described, and detailed descriptions of other portions of such known components will be omitted so as not to obscure the description of the embodiments. In the present specification, an embodiment showing a singular component should not be considered limiting; rather, the scope is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the scope encompasses present and future known equivalents to the components referred to herein by way of illustration.

A sequencing technology would benefit from high throughput, single-molecule reading capability, pure electrical detection and capability with established fabrication processes. The benefits of pure electrical detection include the elimination of bulky and expensive optical detection systems and relatively unstable and expensive fluorescent labeling. The benefits of capability with established fabrication processes include easier integration with other microelectronic devices (e.g., for signal acquisition and processing) and lower production cost.

The term "tag" refers to a marker or indicator distinguishable by an observer. A tag may achieve its effect by undergoing a pre-designed detectable process. Tags are often used in biological assays to be conjugated with, or attached to, an otherwise difficult to detect substance. At the same time, tags usually do not change or affect the underlying assay process. A tag used in biological assays includes, but not limited to, a redox-active molecule.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "sequence" refers to the particular ordering of monomers within a macromolecule and it may be referred to herein as the sequence of the macromolecule.

Figure 1B:
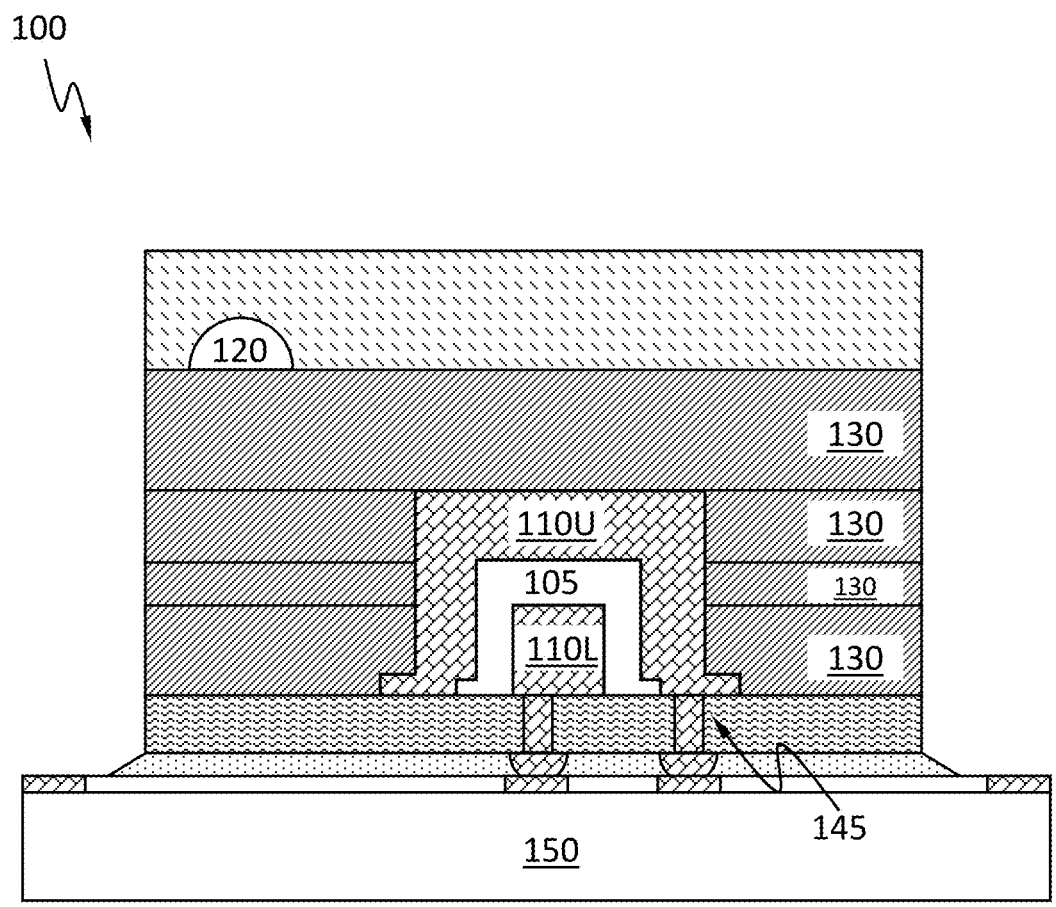
Figure 1C:
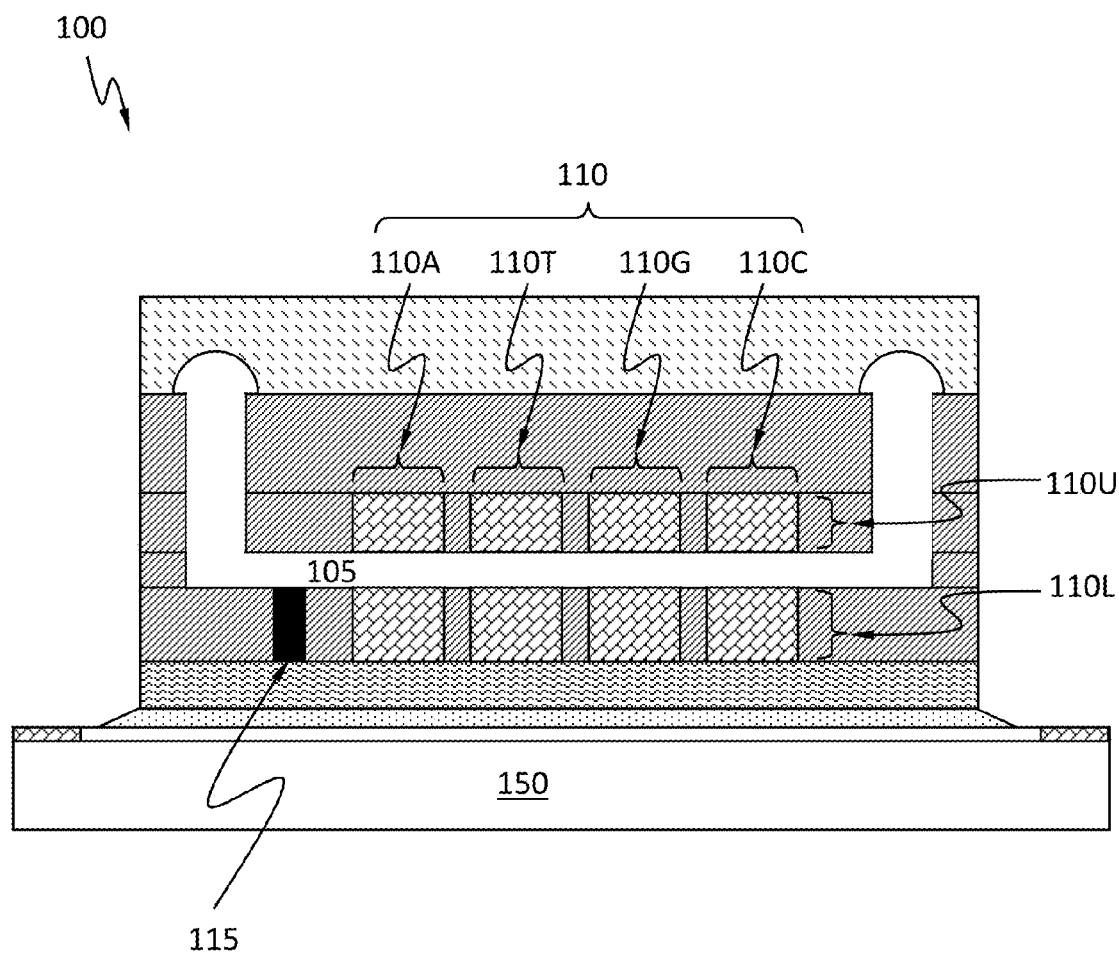

FIG. 1A-FIG. 1C schematically show the structure of a device suitable single molecule 100 sequencing, according to an embodiment. FIG. 1A shows a top view of this device 100. FIG. 1B shows a cross-sectional view along section B. FIG. 1C shows a cross-sectional view along section C. The device 100 has a nanogap channel 105 and a plurality of electrode pairs 110. The device 100 may further have any combination of a bioreactor 115, a bypass channel 120, an inlet 125, and an outlet 135. The plurality of electrode pairs 110 and the nanogap channel 105 may be formed in one or more layers 130 of dielectric materials. The plurality of electrode pairs 110 may be electrically connected to an electric circuit 150 through vias 145.

Each electrode pair among the plurality of electrode pairs 110 comprises a first electrode 110U and a second electrode 110L. The first electrode 110U may include one or more discrete pieces of conductors. The second electrode 110L may include one or more discrete pieces of conductors. A portion of the nanogap channel is sandwiched between the first electrode 110U and the second electrode 110L. At least a portion of the first electrode 110U directly faces at least a portion of the second electrode 110L, across the nanogap channel 105. The distance between these facing portions across the first dimension is 100 nm or less, 75 nm or less, 50 nm or less, 25 nm or less, 10 nm or less, 5 nm or less, or 1 nm or less. At least a portion of the first electrode 110U is exposed to an interior of the nanogap channel 105. At least a portion of the second electrode 110L is exposed to an interior of the nanogap channel 105. The phrase "exposed to an interior of the nanogap channel 105" means that the first electrode 110U, the second electrode 110L and the nanogap channel 105 are arranged such that a fluid filling the interior of the nanogap channel 105 directly contacts the first electrode 110U and the second electrode 110L. The first electrode 110U and the second electrode 110L are electrically conductive. The first electrode 110U and the second electrode 110L can be made of different materials or the same material. The first electrode 110U and the second electrode 110L preferably do not dissolve in water. The first electrode 110U and the second electrode 110L may include gold, platinum, palladium, silver, boron doped diamond and, alloys, mixtures or composites thereof.

The nanogap channel 105 may fluidically and sequentially extend across each of the plurality of electrode pairs 110. The nanogap channel 105 and the plurality of electrode pairs 110 are arranged such that fluid flowing along the nanogap channel 105 passes between the first electrode 110U and the second electrode 110L of one of the electrode pairs 110 before the fluid passes between the first electrode 110U and the second electrode 110L of another of the electrode pairs 110. The nanogap channel 105 is not necessarily straight. A portion of the nanogap channel 105 between the first electrode 110U and the second electrode 110L of an electrode pair among the plurality of electrode pairs 110 may have a height (i.e., the distance separating the first electrode 110U and the second electrode 110L along the first dimension) of 100 nm or less, 75 nm or less, 50 nm or less, 25 nm or less, 10 nm or less, 5 nm or less, or 1 nm or less. The nanogap channel 105 may have a size across a second dimension ("width") (i.e., the dimension perpendicular to the first dimension and the flow direction of the nanogap channel 105) of 500 nm or less, 250 nm or less, 100 nm or less, 50 nm or less, or 10 nm or less. The cross-sectional shape of the nanogap channel 105 perpendicular to the flow direction thereof may be rectangular, square, circular, elliptical or any other suitable shape.

Figure 2:
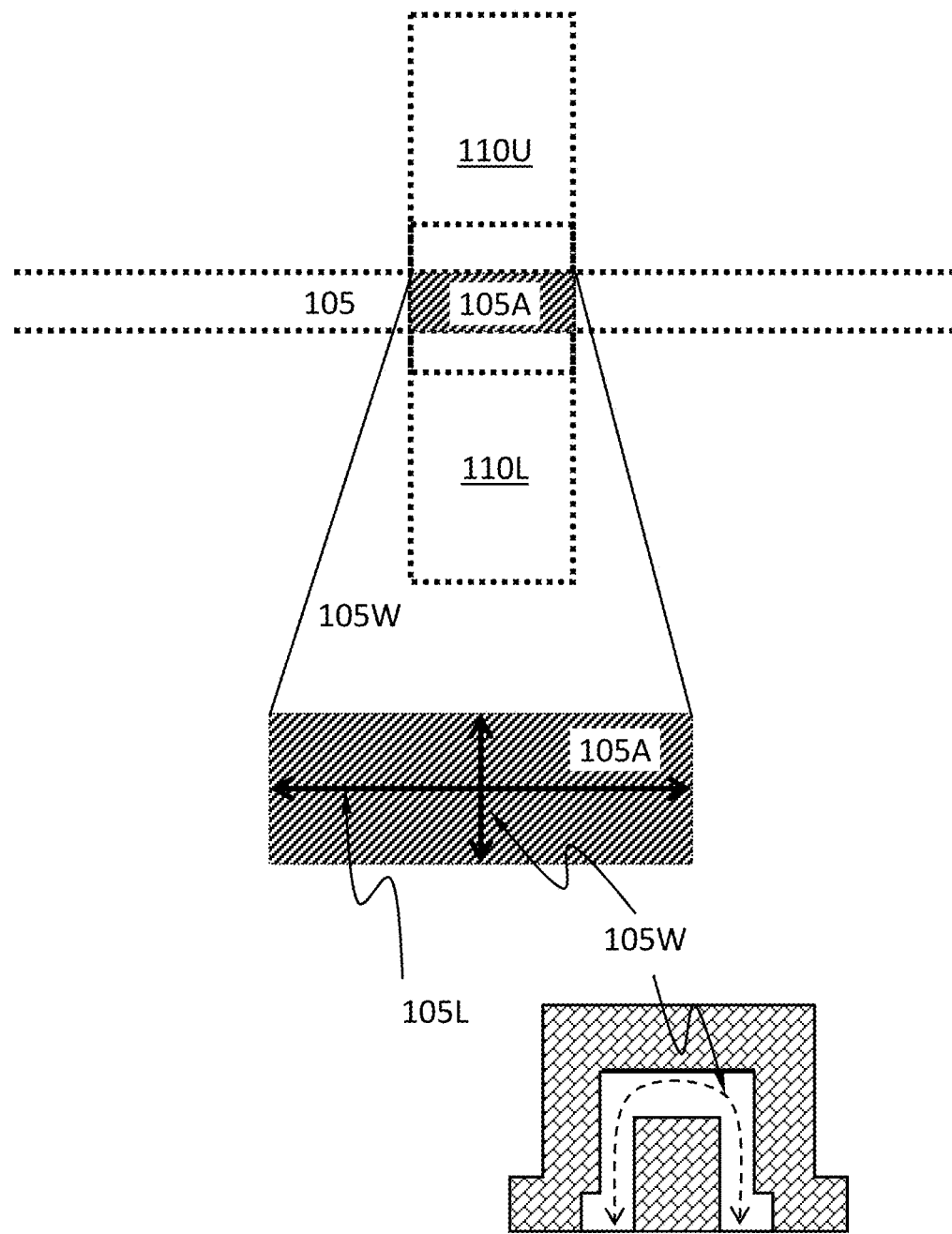
FIG. 2 schematically shows the high length to width ratio of the portion of the nanogap channel sandwiched between the directly facing portions of the electrodes of an electrode pair, according to an embodiment.

As shown in FIG. 2, the portion 105A of the nanogap channel 105 sandwiched between the directly facing portions of the electrodes 110U and 110L preferably has a high length 105L to width 105W ratio. The width can be a distance extending from one end of a cross-section of the nanogap channel 105 perpendicular to the flow direction to the other end (e.g., along the dotted line with two arrow heads). Preferably, the ratio is greater than 50:1, greater than 100:1, greater than 500:1, greater than 1000:1, or greater than 2000:1. Higher length 105L to width 105W ratio leads to more time a redox active molecule stays in the portion 105A and less stray capacitance due to the area of the fluid-electrodes interfaces.

The plurality of electrode pairs 110 are configured to identify chemical species (e.g., four chemical species) passing therebetween and flowing in the nanogap channel 105, for example, by an electrical signal the chemical species generate on the plurality of electrode pairs 110. The electrical signal may be generated from an electrochemical reaction of the chemical species, from a chemical reaction of the chemical species, or a combination thereof. For example, the plurality of electrode pairs 110 may be electrically biased differently in order to identify the chemical species. A chemical species may undergo an electrochemical or chemical reaction at one or more electrical potentials (usually relative to a reference electrode or to the solution the chemical species is in) but not at others. If a first chemical species undergoes a reaction at a first potential and a second chemical species undergoes a reaction at a second potential different from the first potential, an electrode pair biased at the first potential will generate an electrical signal (e.g., voltage or current) when the first chemical species is present regardless whether the second chemical species is present, and an electrode pair biased at the second potential will generate an electrical signal (e.g., voltage or current) when the second chemical species is present regardless whether the first chemical species is present. A chemical species may undergo an electrochemical or chemical reaction with a material attached to an electrode pair but not with another material attached to another electrode pair. If a first chemical species undergoes a reaction with a first material and a second chemical species undergoes a reaction with a second material different from the first material, an electrode pair with the first material attached thereto will generate an electrical signal (e.g., voltage or current) when the first chemical species is present regardless whether the second chemical species is present, and an electrode pair with the second material attached thereto will generate an electrical signal (e.g., voltage or current) when the second chemical species is present regardless whether the first chemical species is present.

The device 100 of FIG. 1A-1C may be used to sequence peptides, DNAs and RNAs. DNA sequencing is used as an example to explain the operation of this device.

Figure 3:
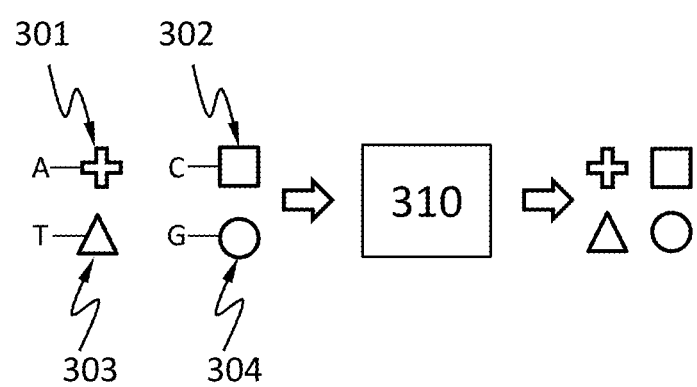
FIG. 3 schematically shows that the plurality of electrode pairs may be configured to identify products of incorporation reactions of nucleotides (e.g., dATP, dTTP, dGTP, and dCTP) into a complementary strand to a DNA molecule being sequenced, according to an embodiment.

In the context of DNA sequencing, the plurality of electrode pairs 110 may be configured to identify products of incorporation reactions of nucleotides (e.g., dATP, dTTP, dGTP, and dCTP) into a complementary strand to a DNA molecule being sequenced, as schematically shown in FIG. 3. The reaction products may be a distinct tag 301, 302, 303 or 304 on each type (e.g., A, T, G, C) of the nucleotides introduced to react with the complementary strand, where upon incorporation 310 of the nucleotides, the distinct tag 301, 302, 303 or 304 is released from the nucleotides and can flow to the plurality of electrode pairs 110. The released tag may be "activated," e.g., by using activating enzymes or other molecules, before flowing to the plurality of electrode pairs 110. Upon identifying the released tag by the plurality of electrode pairs 110, the type of the nucleotide incorporated is ascertained.

Alternatively, the plurality of electrode pairs 110 may be configured to identify products of digestion of a DNA molecule being sequenced. For example, the DNA molecule being sequenced may be digested by a nuclease to sequentially release the nucleosides or nucleotides in the DNA molecule. The released nucleosides or nucleotides flow to the plurality of electrode pairs 110 and are identified by them. Alternatively, the released nucleosides or nucleotides may be "activated," e.g., by using activating enzymes or other molecules, to produce distinct tags that flow to the plurality of electrode pairs 110 and are identified by them. Upon identifying the released nucleosides or nucleotides or the tags by the plurality of electrode pairs 110, the type of the nucleotide incorporated is ascertained.

The plurality of electrode pairs 110 may have two, three, four, or more electrode pairs. The plurality of electrode pairs 110 are preferably independently addressable. In one embodiment, the plurality of electrode pairs 110 have four electrode pairs 110A, 110T, 110G and 110C. For example, electrode pairs 110A, 110T, 110G and 110C are configured (by biasing at four different potentials or by attaching with four different materials) such that they generate a signal when a tag released (or also activated) from incorporation of dATP, dTTP, dGTP or dCTP is present, respectively, or such that they generate a signal when an adenosine (or a deoxyadenosine), a thymidine (or a deoxythymidine), a guanosine (or a deoxyguanosine), a cytidine (or a deoxycytidine) released (or also activated) from digestion is present, respectively.

Figure 1D:
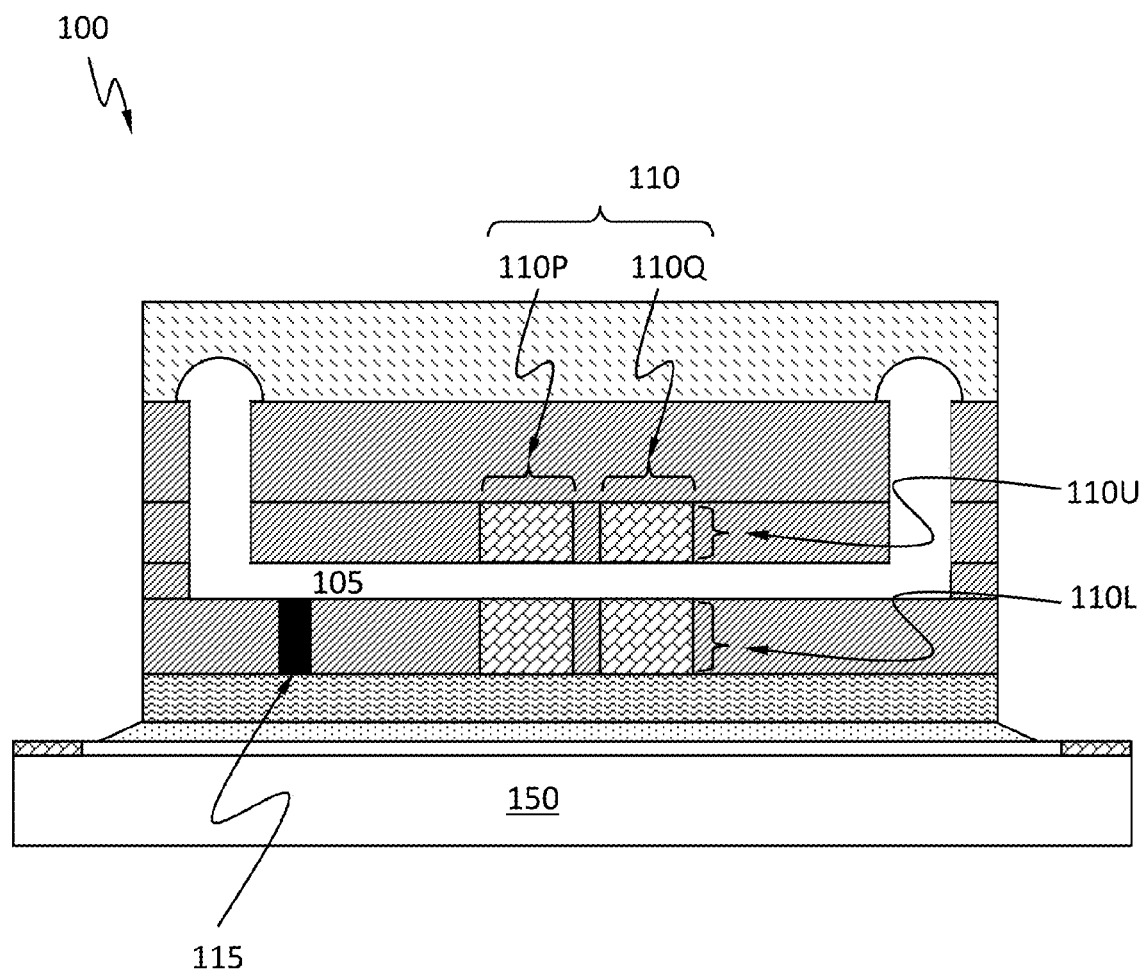

In one embodiment, as shown in FIG. 1D, the plurality of electrode pairs 110 have two electrode pairs 110P and 110Q. For example, electrode pairs 110P, and 110Q are configured (by biasing at two different potentials or by attaching with two different materials) such that electrode pair 110P generates a signal when a tag released (or also activated) from incorporation of a dTTP or dCTP is present; and such that electrode pair 110Q generates a signal when a tag released (or also activated) from incorporation of a dTTP or dATP is present.

Figure 1E:
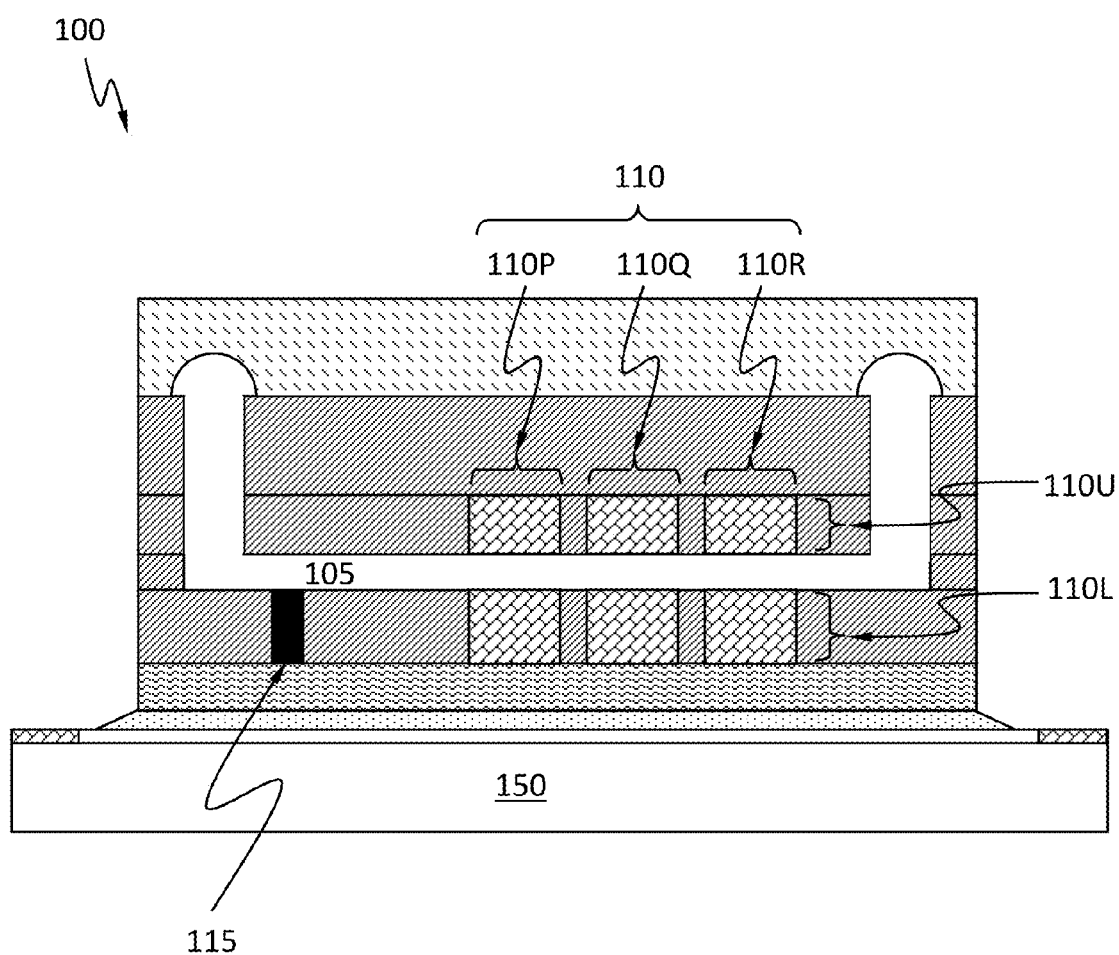

In one embodiment, as shown in FIG. 1E, the plurality of electrode pairs 110 have three electrode pairs 110P, 110Q and 110R. For example, electrode pairs 110P, 110Q and 110R are configured (by biasing at three different potentials or by attaching with three different materials) such that electrode pair 110P generates a signal when a tag released (or also activated) from incorporation of a dTTP or dCTP is present; such that electrode pair 110Q generates a signal when a tag released (or also activated) from incorporation of a dTTP or dATP is present; and such that electrode 110R generates a signal when a tag released (or also activated) from incorporation of a dATP, dTTP, dGTP or dCTP is present.

Figure 4:
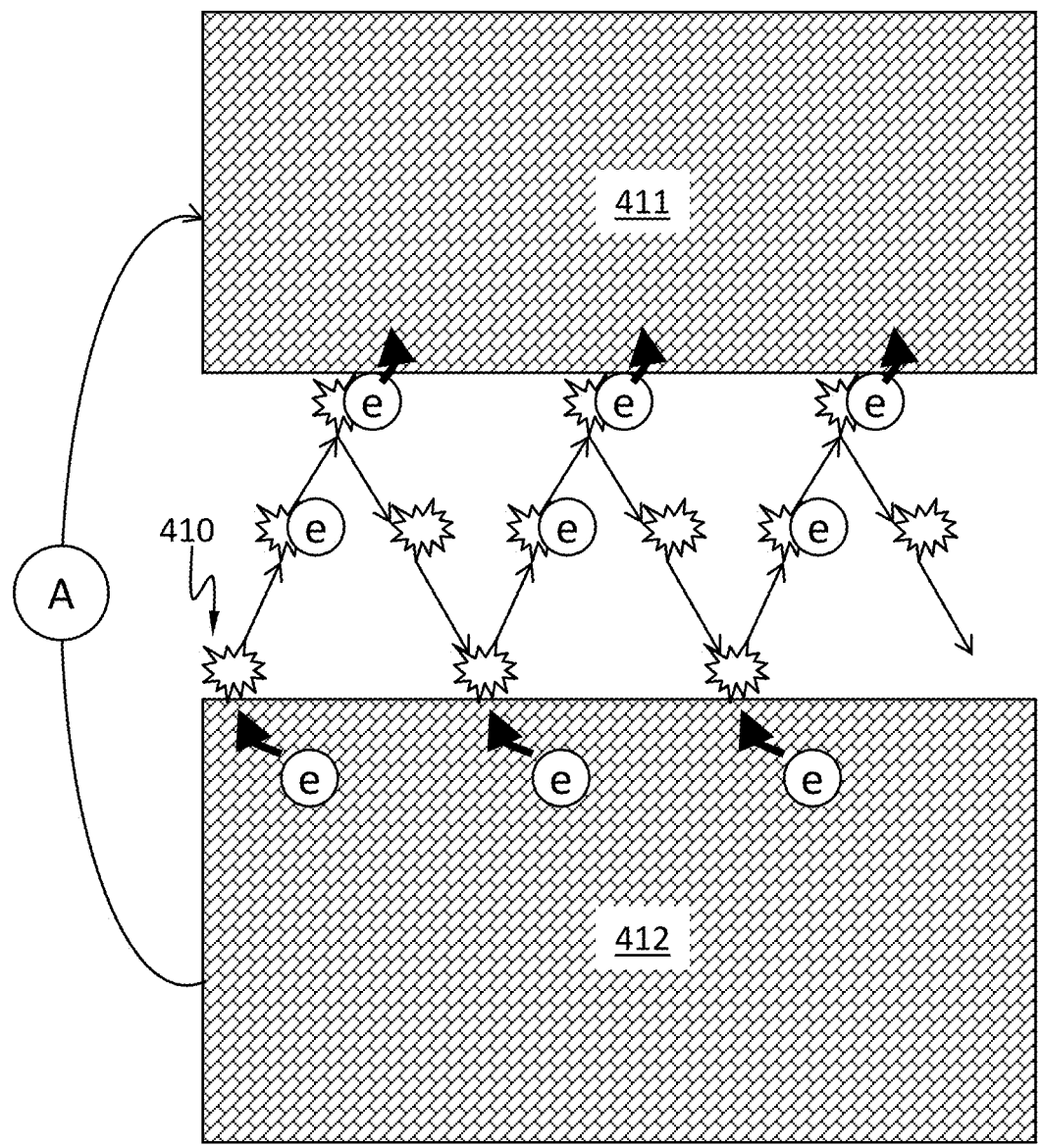
FIG. 4 schematically shows redox cycling, according to an embodiment.

In an embodiment, identification of a chemical species by an electrode pair involves redox cycling. Redox cycling can be especially useful when only a few or even a single molecule of the chemical species are available for identification. FIG. 4 schematically shows redox cycling. Redox cycling is an electrochemical method in which a molecule 410 that can be reversibly oxidized and/or reduced (i.e., a redox active molecule) moves between at least two electrodes 411 and 412, one of which biased below a reduction potential and the other of which biased above an oxidation potential for the molecule being detected, shuttling electrons between the electrodes (i.e., the molecule is oxidized at a first electrode 411 and then diffuses to a second electrode 412 where it is reduced or vice versa, it is first reduced and then oxidized, depending on the molecule and the potentials at which the electrodes are biased). The same molecule 410 can therefore contribute a plurality of electrons to the recorded current resulting in the net amplification of the signal (e.g., presence of molecule 410). In a redox cycling measurement, the electrodes 411 and 412 are used to repeatedly flip the charge state of a redox active molecule 410 in solution allowing a single redox active molecule to participate in multiple redox reactions and thereby contribute multiple electrons to an electric current between the electrodes 411 and 412. In redox cycling measurements, the height of the gap between the electrodes 411 and 412 can be on the nanometer scale. In the device of FIG. 1A-FIG. 1C, the height of the gap is the height of the nanogap channel 105. A single redox active molecule 410 flowing between the two electrodes 411 and 412 can shuttle multiple electrons (e.g., >100) between the electrodes 411 and 412, leading to amplification of the measured electrochemical current. The number of electrons a single redox active molecule 410 can shuttle depends on factors such as the stability of the redox active molecule 410 and the time the redox active molecule 410 spends in the region between the electrodes 411 and 412. The magnitude of current through either electrode is proportional to the concentration of the redox active molecule 410 in the region between the electrodes 411 and 412 and to the number of electrons the redox active molecule 410 shuttles from one electrode to the other. In the device of FIG. 1A-FIG. 1C, the number of electrons shuttled from one electrode to the other electrode of an electrode pair by one redox active molecule 410 may depend on the length of the portion of the nanogap channel 105 sandwiched by the electrode pair. A redox active molecule is a molecule that is capable of reversibly cycling through states of oxidation and/or reduction a plurality of times.

According to an embodiment, the bioreactor 115 may be arranged such that all reaction products from the bioreactor 115 flow into the nanogap channel 105 and by the plurality of electrode pairs 110. The bioreactor 115 may be positioned inside the nanogap channel 105 and upstream to the plurality of electrode pairs 110. The bioreactor 115 is not necessarily inside the nanogap channel 105. The bioreactor 115 may be an area with a functionalized surface. The bioreactor 115 may be an area of different materials from its surrounding areas. For example, the bioreactor 115 may be an area of silicon oxide or gold. Being an area made of a different material makes surface functionalization easier. For example, if the bioreactor 115 is the only component made of gold that is exposed to the interior of the nanogap channel 105, the surface of the bioreactor 115 can be modified by flowing a ligand that only reacts with gold through the nanogap channel 105. The functionalized surface may be used as a site to immobilize a molecule thereon. The molecule may be a polymerase, a nuclease, a DNA or RNA strand, or a peptide. The bioreactor 115 preferably has a small area (e.g., 100 nm or less in diameter) so that statistically only one molecule is immobilized thereon.

A flow through the nanogap channel 105 may be induced. The flow preferably transports reaction products from the bioreactor 115 through the nanogap channel 105 sequentially, in an order of time of release (e.g., dissociation from any immobilized molecule into the flow) of the reaction products. Namely, the flow transports a reaction product released earlier before a reaction product released later. The flow preferably is at a rate that preserves the order of the reaction products before they pass the last electrode pair. The flow rate may be as low as in the range of pl/min (picoliters per minute). The flow may be induced by a pressure differential between the inlet 125 and the outlet 135. When the pressure differential dictated by the desired flow rate is too small to be practically maintained, the device 100 can have a bypass channel 120 fluidically parallel with the nanogap channel 105. For example, if the practically maintainable flow rate is in the range of µl/min. The bypass channel 120 can be much wider than the nanogap channel 105 so that the fraction through the latter is at a much smaller flow rate. The bypass channel 120 may have a valve that can controllably shut it off.

The electric circuit 150 may be a chip of CMOS electronics. The rest of the device 100 may be attached to the electric circuit 150 by a suitable technique such as solder microbumps.

The electric circuit 150 may have the sensitivity and foot print size to match the density of the electrode pairs. Multiple electrode pairs may share the same circuit. The electric circuit 150 may be configured to read or process signals on the electrode pairs. In an embodiment, the electric circuit 150 is configured to read a differential of the potential on the first electrode 110U and the second electrode 110L of an electrode pair (e.g., FIG. 5A). In an embodiment, the electric circuit 150 is configured to use transimpedance amplifiers to amplify the signal by cross-correlation signal processing techniques to reduce the amplifier noise (e.g., FIG. 5B). In an embodiment, the electric circuit 150 is configured to allow sharing of the circuit among multiple electrode pairs (e.g., FIG. 5C) in a time domain multiplexed fashion.

Figure 5A:
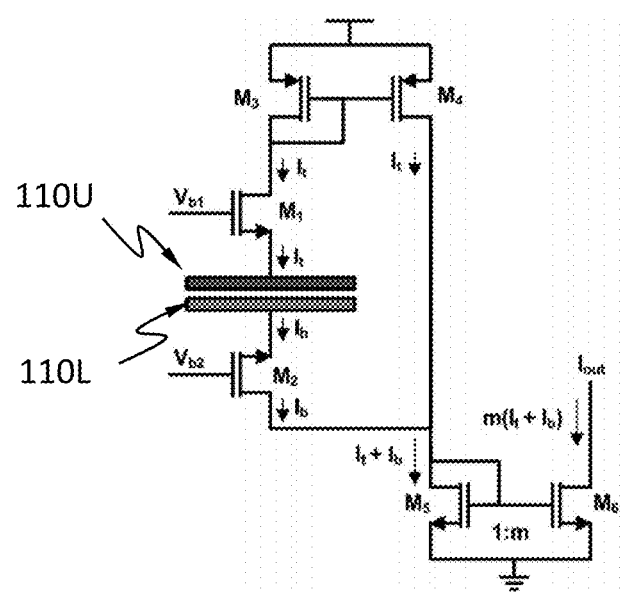
FIG. 5A-5D show various electric circuits that can be used to read and process signals from the electrode pairs, according to an embodiment.

FIG. 5A is an example of the electric circuit 150 that uses two common gate amplifiers (M1 and M2) which set the electrode potentials approximately Vb1-Vt and Vb2-Vt (Vt is the threshold voltage) while relaying the electrode current to either a current mirror formed by M3/M4 (which inverts it) or to the summing node directly. The current mirror formed by M5 and M6 provides amplification and an interface to a current-mode ADC or other means of acquiring the resulting current, which can be shared between many electrode pairs.

Figure 5B:
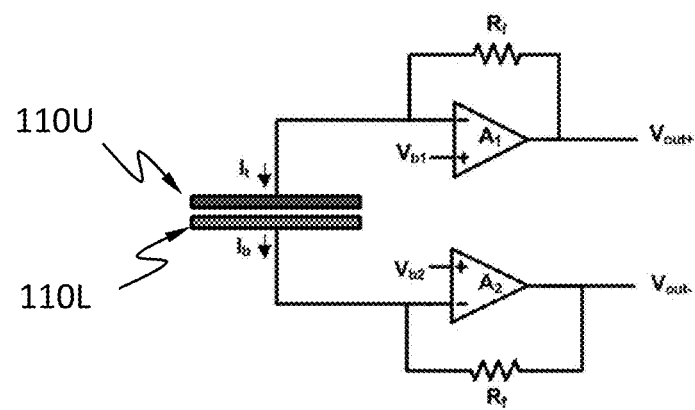

FIG. 5B is an example of the electric circuit 150 that independently acquires signals from both electrodes so that cross-correlation signal processing techniques can be used to reduce the impact of the amplifier (A1 and A2) noises.

Figure 5C:
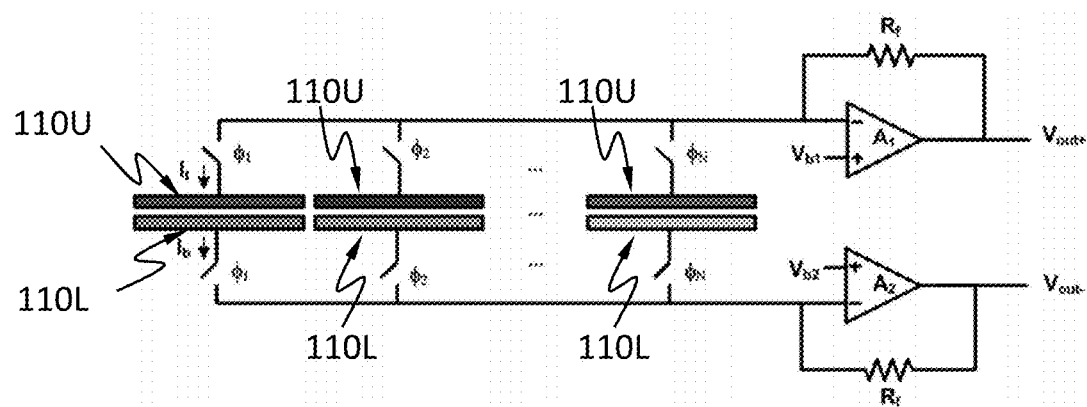

FIG. 5C is an extension of the readout circuit in FIG. 5B, where the amplifiers are shared among many electrode pairs. Switches controlled by non-overlapping control signals may be used to address each of the electrode pairs.

Figure 5D:
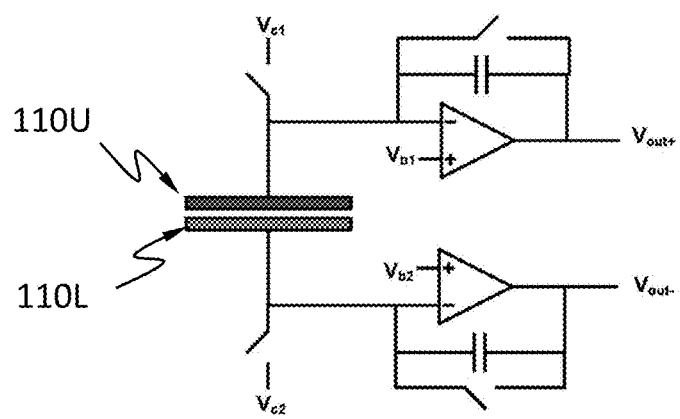

FIG. 5D is a switched capacitor implementation of a pair of transimpedance amplifiers with two separate outputs, which can be used for cross-correlation or similar signal processing. Furthermore, the other switches (e.g., V01, V02) can implement controllable current cancellation (switches can either be connected to a voltage source or to a capacitor). By means of logic controlling the switches, it is possible to implement hardware subtraction or detection of anti-correlated currents at the electrodes. As shown in FIG. 5D, a switched capacitor approach can be used to implement the transimpedance amplifier as well as perform background subtraction of the current traces (to ideally remove any portion not attributable to the redox active molecules) as well as implementing some level of cross-correlation in the circuitry.

Preferably, a redox active molecule that is oxidized or reduced at one of the electrodes 110U and 110L diffuses to the other electrode to complete the redox cycling. However, if the redox active molecule diffuses to some place other than the other electrode, the redox cycling is broken, which causes noise in the signal. Preferably, the electrode pairs are configured such that the redox active molecule can only diffuse back and forth between the electrodes 110U and 110L while it is in the portion of the nanogap channel 105 sandwiched therebetween. If the width of the nanogap channel 105 is not larger than the width of the directly facing portions of the electrodes and is entirely sandwiched between the directly facing portions, the redox cycling is not broken because the redox active molecule can only diffuse back and forth between the electrodes 110U and 110L.

FIGS. 6A-6F show an exemplary fabrication method for the device 100. This method requires at least three lithography processes for the first electrode 110U, the second electrode 110L and the nanogap channel 105, respectively.

Figure 6A:
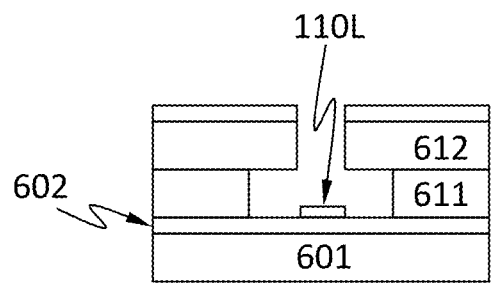
FIGS. 6A-6F show an exemplary fabrication method for the device in FIGS. 1A-1E, according to an embodiment.
Figure 6B:
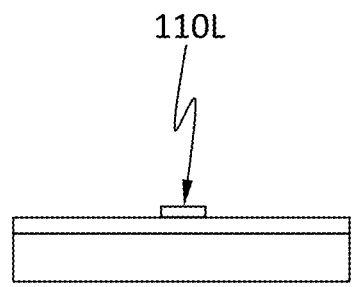

As shown in FIG. 6A and FIG. 6B, the second electrode 110L is patterned on a layer 602 of insulator (e.g., silicon oxide) on a substrate 601 (e.g., silicon wafer) by photolithography. The second electrodes 110L may be platinum, boron doped diamond (BDD), gold or other suitable electrical conductive materials. The second electrodes 110L may be patterned using a suitable technique such as photolithography, e-beam evaporation or sputter deposition through an opening of one or more resist layers 611 (e.g., LOL photo resist) and 612 (e.g., 3612 photoresist), and lift-off (FIG. 6B, the one or more resist layer and any materials thereon removed). An adhesion layer such as titanium (Ti) may be deposited before depositing the second electrodes 110L. If the second electrodes 110L comprise BDD, it may be deposited using chemical vapor deposition (CVD) and may be patterned using a hard mask, such as chromium (Cr), followed by an oxygen plasma etch and Cr removal using CR14 etchant.

Figure 6C:
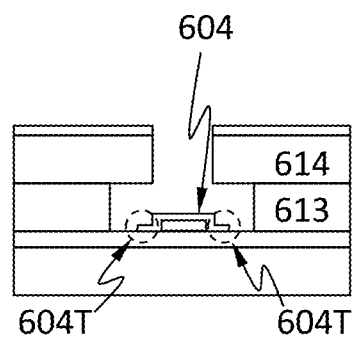
Figure 6D:
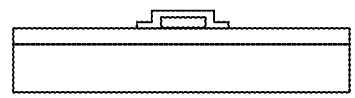

As shown in FIG. 6C and FIG. 6D, a sacrificial layer 604 is patterned on the second electrodes 110L and on the layer 602 of insulator. The sacrificial layer 604 will later be removed to form the nanogap channel 105. The sacrificial layer 604 may be patterned using suitable techniques such as photolithography, metal deposition through an opening of one or more resist layers 613 (e.g., LOL photo resist) and 614 (e.g., 3612 photoresist), and lift-off (FIG. 6D, the one or more resist layer and any materials thereon removed). Chromium (Cr), tantalum nitride (TaN) and tungsten (W) are examples of the material of the sacrificial layer 604 due to their capability of being selectively etched compared to the other materials in the device 100. In order to prevent short circuit between the first electrode 110U and the second electrode 110L, and to accommodate misalignment between the lithography process for the first electrode 110L and the lithography process for the second electrode 110U, the sacrificial layer 604 not only conformally covers the second electrode 110L but also has tails 604T extending away from the second electrode 110L. When the sacrificial layer 604 is later removed to form the nanogap channel 105, the void space left by the tails 604T would only have the first electrode 110U but not the second electrode 110L exposed to its interior. If the redox active molecule diffuses to this void space, the redox cycling is broken, which causes noise in the signal.

Figure 6E:
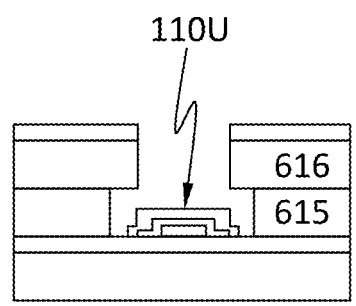
Figure 6F:
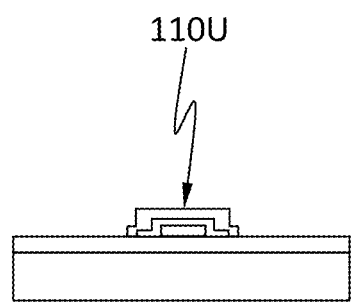

As shown in FIG. 6E and FIG. 6F, the first electrode 110U is patterned on the layer 602 of insulator and on the sacrificial layer 604. The first electrode 110U may be platinum, boron doped diamond (BDD), gold or other suitable electrical conductive materials. The first electrode 110U may be patterned using a suitable technique such as photolithography, e-beam evaporation or sputter deposition through an opening of one or more resist layers 615 (e.g., LOL photo resist) and 616 (e.g., 3612 photoresist), and lift-off (FIG. 6F, the one or more resist layer and any materials thereon removed). An adhesion layer such as titanium (Ti) may be deposited before depositing the first electrode 110U. If the first electrode 110U comprise BDD, it may be deposited using chemical vapor deposition (CVD) and may be patterned using a hard mask, such as chromium (Cr), followed by an oxygen plasma etch and Cr removal using CR14 etchant.

FIGS. 7A-7D show an exemplary fabrication method for the device 100. This method requires only one lithography process for the first electrode 110U, the second electrode 110L and the nanogap channel 105.

Figure 7A:
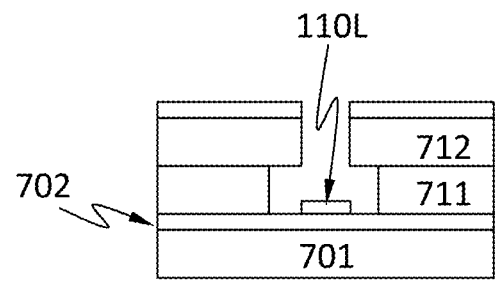
FIGS. 7A-7D show an exemplary fabrication method for the device in FIGS. 1A-1E, according to an embodiment.

As shown in FIG. 7A, the second electrode 110L is patterned on a layer 702 of insulator (e.g., silicon oxide) on a substrate 701 (e.g., silicon wafer) by photolithography. The second electrodes 110L may be platinum, boron doped diamond (BDD), gold or other suitable electrical conductive materials. The second electrodes 110L may be patterned using a suitable technique such as photolithography and directional deposition technique (e.g., e-beam evaporation or thermal evaporation) through an opening of one or more resist layers 711 (e.g., LOL photo resist) and 712 (e.g., 3612 photoresist), without lift-off. An adhesion layer such as titanium (Ti) may be deposited before depositing the second electrodes 110L. If the second electrodes 110L comprise BDD, it may be deposited using chemical vapor deposition (CVD) and may be patterned using a hard mask, such as chromium (Cr), followed by an oxygen plasma etch and Cr removal using CR14 etchant.

Figure 7B:
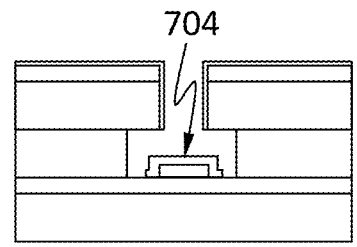

As shown in FIG. 7B, a strip of a sacrificial layer 704 is patterned on the second electrodes 110L and on the layer 702 of insulator. The sacrificial layer 704 will later be removed to form the nanogap channel 105. The sacrificial layer 704 may be deposited using a non-directional deposition technique (e.g., sputtering) through the same opening of the same resist layers 711 (e.g., LOL photo resist) and 712 (e.g., 3612 photoresist) without lift-off. The sacrificial layer 704 conformally covers the entire second electrode 110L so as to isolated it from the first electrode 110U to be deposited next. Chromium (Cr), tantalum nitride (TaN) and tungsten (W) are examples of the material of the sacrificial layer 704 due to their capability of being selectively etched compared to the other materials in the device 100. Because this method uses only one lithography process for the first electrode 110U and the second electrode 110L and the sacrificial layer 704, misalignment between the lithography processes exists. The sacrificial layer 704 thus can avoid having large tails extending away from the second electrode 110L to accommodate such misalignment. When the sacrificial layer 704 is later removed to form the nanogap channel 105, the nanogap channel 105 would have none or very little void space left by any tails of the sacrificial layer 704. Therefore, the redox active molecule has no or little chance of diffusing to this space and the redox cycling will not or will unlikely be broken. The noise in the signal on the electrode pair 110 is thus reduced.

Figure 7C:
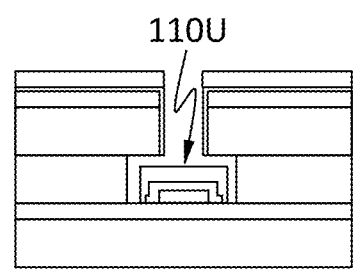
Figure 7D:
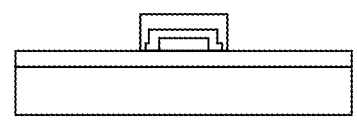

As shown in FIG. 7C, the first electrode 110U is patterned on the layer 702 of insulator and on the sacrificial layer 704. The first electrode 110U may be platinum, boron doped diamond (BDD), gold or other suitable electrical conductive materials. The first electrode 110U may be deposited using a non-directional deposition technique (e.g., sputtering) through the same opening of the same resist layers 711 (e.g., LOL photo resist) and 712 (e.g., 3612 photoresist) with lift-off (FIG. 7D, the resist layers and any materials thereon removed, leaving only the first electrode 110U, the sacrificial layer 702 and the second electrode 110L). An adhesion layer such as titanium (Ti) may be deposited before depositing the first electrode 110U. If the first electrode 110U comprise BDD, it may be deposited using chemical vapor deposition (CVD) and may be patterned using a hard mask, such as chromium (Cr), followed by an oxygen plasma etch and Cr removal using CR14 etchant. The first electrode 110U may conformally cover the sacrificial layer 704.

Figure 8:
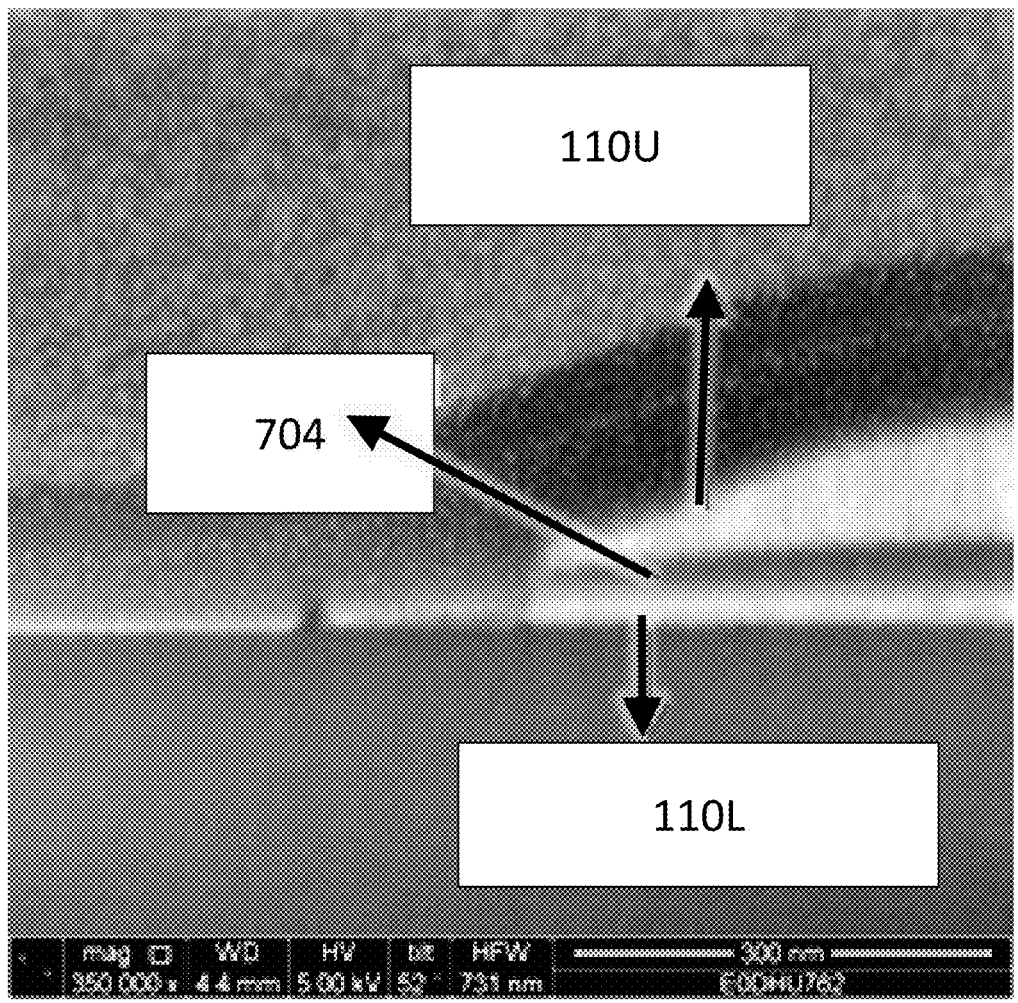
FIG. 8 shows an exemplary cross-sectional image obtained by scanning electron microscopy (SEM) from the device fabricated using the method including the method of FIGS. 7A-7D, according to an embodiment.

FIG. 8 shows an exemplary cross-sectional image obtained by scanning electron microscopy (SEM) from the device fabricated using the method of FIGS. 7A-7D.

FIGS. 9A-9D show an exemplary fabrication method for the device 100, similar to the method in FIGS. 7A-7D. This method requires only one lithography process for the first electrode 110U, the second electrode 110L and the nanogap channel 105.

Figure 9A:
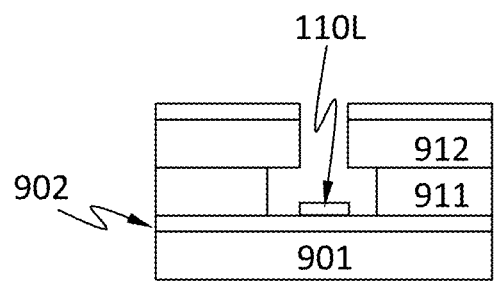
FIGS. 9A-9D show an exemplary fabrication method for the device in FIGS. 1A-1E, according to an embodiment.

As shown in FIG. 9A, the second electrode 110L is patterned on a layer 902 of insulator (e.g., silicon oxide) on a substrate 901 (e.g., silicon wafer) by photolithography. The second electrodes 110L may be platinum, boron doped diamond (BDD), gold or other suitable electrical conductive materials. The second electrodes 110L may be patterned using a suitable technique such as photolithography and directional deposition technique (e.g., e-beam evaporation or thermal evaporation) through an opening of one or more resist layers 911 (e.g., LOL photo resist) and 912 (e.g., 3612 photoresist), without lift-off. An adhesion layer such as titanium (Ti) may be deposited before depositing the second electrodes 110L. If the second electrodes 110L comprise BDD, it may be deposited using chemical vapor deposition (CVD) and may be patterned using a hard mask, such as chromium (Cr), followed by an oxygen plasma etch and Cr removal using CR14 etchant.

Figure 9B:
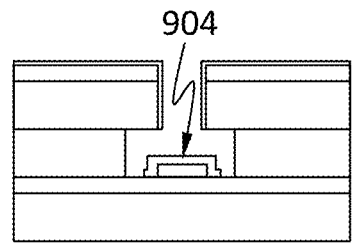

As shown in FIG. 9B, a strip of a sacrificial layer 904 is patterned on the second electrodes 110L and on the layer 902 of insulator. The sacrificial layer 904 will later be removed to form the nanogap channel 105. The sacrificial layer 904 may be deposited using a non-directional deposition technique (e.g., sputtering) through the same opening of the same resist layers 911 (e.g., LOL photo resist) and 912 (e.g., 3612 photoresist) without lift-off. The sacrificial layer 904 conformally covers the entire second electrode 110L so as to isolated it from the first electrode 110U to be deposited next. Chromium (Cr), tantalum nitride (TaN) and tungsten (W) are examples of the material of the sacrificial layer 904 due to their capability of being selectively etched compared to the other materials in the device 100.

Figure 9C:
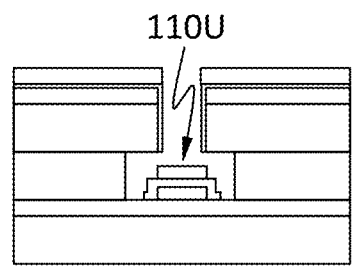
Figure 9D:
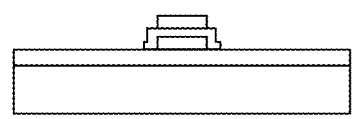

As shown in FIG. 9C, the first electrode 110U is patterned on the layer 902 of insulator and on the sacrificial layer 904. The first electrode 110U may be platinum, boron doped diamond (BDD), gold or other suitable electrical conductive materials. The first electrode 110U may be deposited using a directional deposition technique (e.g., e-beam evaporation or thermal evaporation) through the same opening of the same resist layers 911 (e.g., LOL photo resist) and 912 (e.g., 3612 photoresist) with lift-off (FIG. 9D, the resist layers and any materials thereon removed, leaving only the first electrode 110U, the sacrificial layer 902 and the second electrode 110L). An adhesion layer such as titanium (Ti) may be deposited before depositing the first electrode 110U. If the first electrode 110U comprise BDD, it may be deposited using chemical vapor deposition (CVD) and may be patterned using a hard mask, such as chromium (Cr), followed by an oxygen plasma etch and Cr removal using CR14 etchant. Because the first electrode 110U and the second electrode 110L are deposited through the same opening of the resist layers, they are automatically aligned. The first electrode 110U may not cover the entire sacrificial layer 904.

Figure 10:
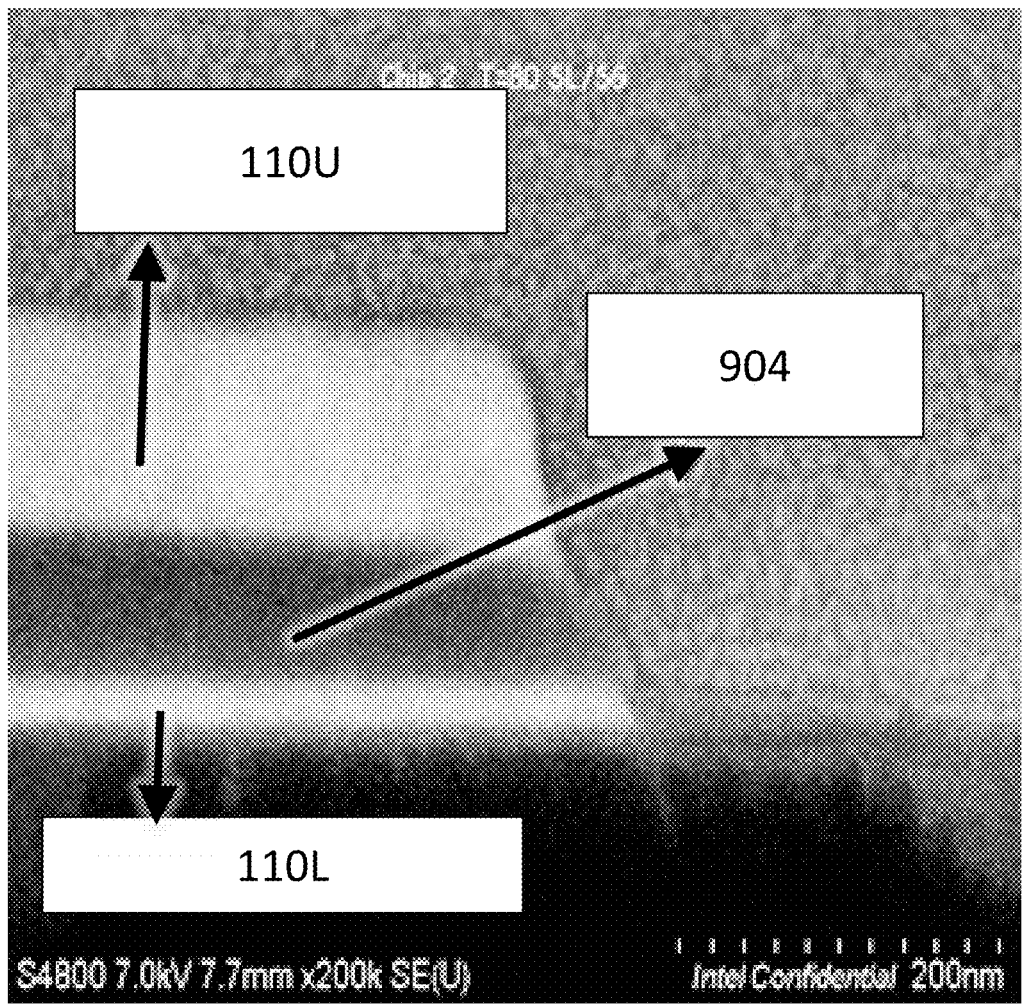
FIG. 10 shows an exemplary cross-sectional image obtained by SEM from the device fabricated using the method including the method of FIGS. 9A-9D, according to an embodiment.

FIG. 10 shows an exemplary cross-sectional image obtained by SEM from the device fabricated using the method including the method of FIGS. 9A-9D.

FIGS. 11A-11E show an exemplary fabrication method for the device 100. This method requires only one lithography process for the first electrode 110U, the second electrode 110L and the nanogap channel 105.

As shown in FIG. 11A, the second electrode 110L is patterned on a layer 1102 of insulator (e.g., silicon oxide) on a substrate 1101 (e.g., silicon wafer) by photolithography. The second electrodes 110L may be platinum, boron doped diamond (BDD), gold or other suitable electrical conductive materials. The second electrodes 110L may be patterned using a suitable technique such as photolithography and directional deposition technique (e.g., e-beam evaporation or thermal evaporation) through an opening of one or more resist layers 1111 (e.g., LOL photo resist) and 1112 (e.g., 3612 photoresist), without lift-off. A layer 1180 of the materials of the second electrode 110L are also deposited on top of the resist layers, and will be later removed together with the resist layers during lift-off. An adhesion layer such as titanium (Ti) may be deposited before depositing the second electrodes 110L. If the second electrodes 110L comprise BDD, it may be deposited using chemical vapor deposition (CVD) and may be patterned using a hard mask, such as chromium (Cr), followed by an oxygen plasma etch and Cr removal using CR14 etchant. A layer 1180 of the materials of the second electrode 110L are also deposited on top of the resist layers, and will be later removed together with the resist layers during lift-off.

As shown in FIG. 11B, the opening of the resist layers 1111 and 1112 are isotropically enlarged by a suitable method (e.g., oxygen plasma). The layer 1180 on top of the resist layers may remain and function as a shadow mask for later processes.

As shown in FIG. 11C, a strip of a sacrificial layer 1104 is patterned on the second electrodes 110L and on the layer 1102 of insulator. The sacrificial layer 1104 will later be removed to form the nanogap channel 105. The sacrificial layer 1104 may be deposited using a non-directional deposition technique (e.g., sputtering) through the same opening of the same resist layers 1111 (e.g., LOL photo resist) and 1112 (e.g., 3612 photoresist) without lift-off. The sacrificial layer 1104 conformally covers the entire second electrode 110L so as to isolated it from the first electrode 110U to be deposited next. Chromium (Cr), tantalum nitride (TaN) and tungsten (W) are examples of the material of the sacrificial layer 1104 due to their capability of being selectively etched compared to the other materials in the device 100.

As shown in FIG. 11D, the first electrode 110U is patterned on the layer 1102 of insulator and on the sacrificial layer 1104. The first electrode 110U may be platinum, boron doped diamond (BDD), gold or other suitable electrical conductive materials. The first electrode 110U may be deposited using a directional deposition technique (e.g., e-beam evaporation or thermal evaporation) through the enlarged opening of the same resist layers 1111 (e.g., LOL photo resist) and 1112 (e.g., 3612 photoresist), or through the opening in the layer 1080 corresponding to the opening of the resist layers before enlargement, with lift-off (FIG. 11E, the resist layers and the layer 1080 thereon removed, leaving only the first electrode 110U, the sacrificial layer 1102 and the second electrode 110L). An adhesion layer such as titanium (Ti) may be deposited before depositing the first electrode 110U. If the first electrode 110U comprise BDD, it may be deposited using chemical vapor deposition (CVD) and may be patterned using a hard mask, such as chromium (Cr), followed by an oxygen plasma etch and Cr removal using CR14 etchant. Because the first electrode 110U and the second electrode 110L are deposited through the isotropically enlarged opening of the resist layers or through the opening in the layer 1080 corresponding to the opening of the resist layers before enlargement, the first electrode 110U and the second electrode 110L are automatically aligned. The first electrode 110U may not cover the entire sacrificial layer 904.

Figure 12:
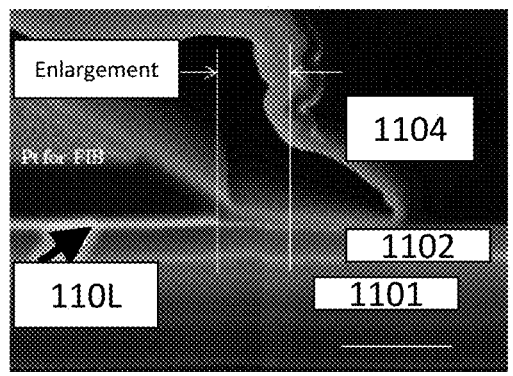
FIG. 12 shows an exemplary cross-sectional image obtained by SEM from the device fabricated using the method including the method of FIGS. 11A-11E, according to an embodiment.

FIG. 12 shows an exemplary cross-sectional image obtained by SEM from the device fabricated using the method including the method of FIGS. 11A-11E.

Figure 13A:
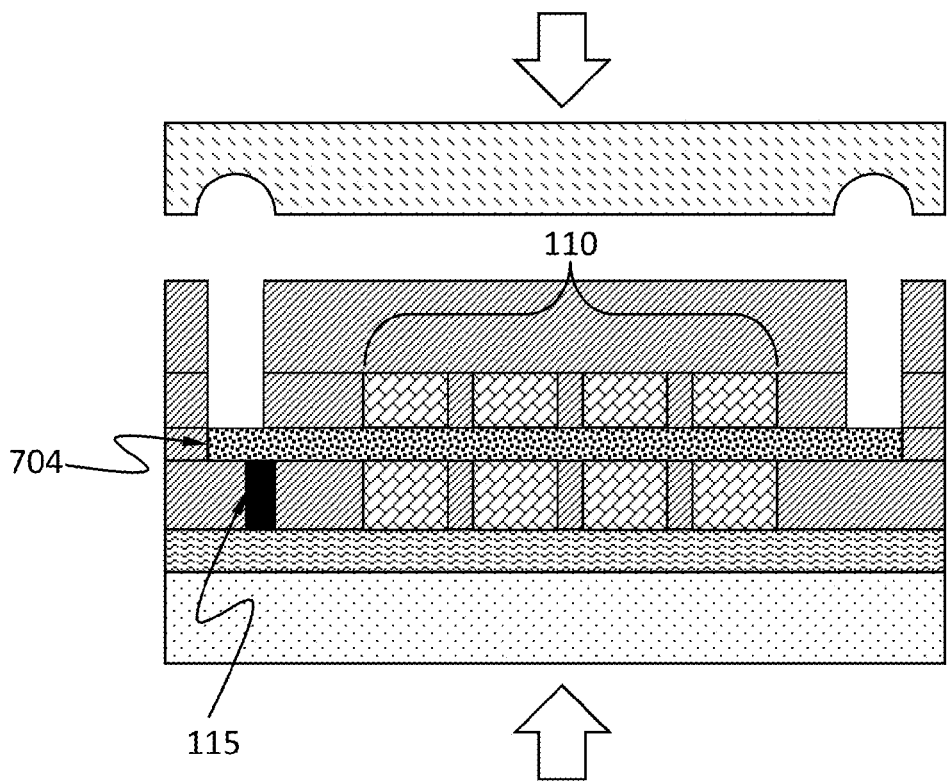
FIG. 13A and FIG. 13B show an exemplary method of bonding a microfluidics chip, according to an embodiment.
Figure 13B:
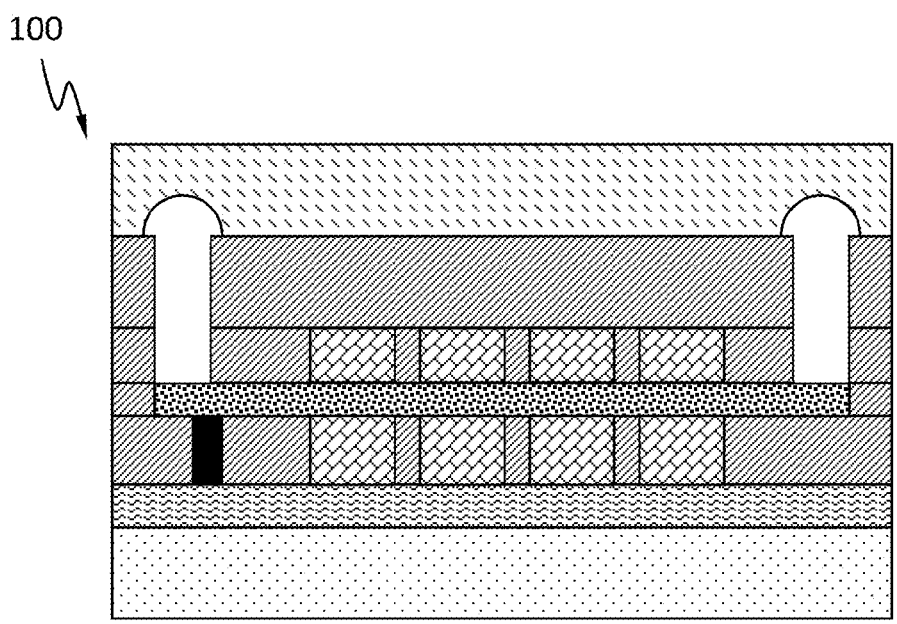
Figure 15A:
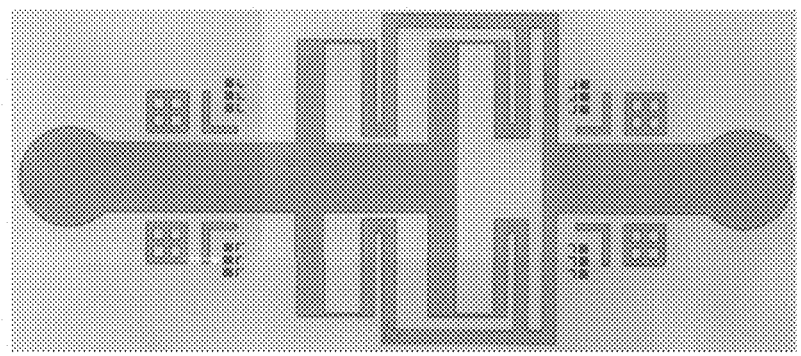
FIG. 15A and FIG. 15B show a top view image of a microfluidic network and its overlay with the nanogap device, according to an embodiment.
Figure 15B:
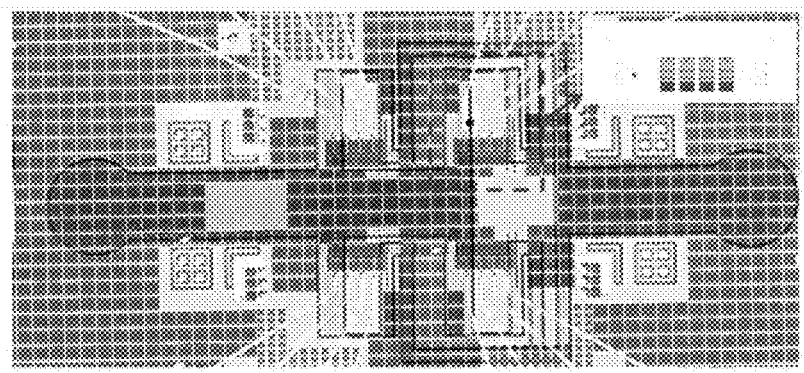

FIG. 13A and FIG. 13B show an exemplary method of bonding a microfluidics chip (e.g., on a borosilicate wafer) including the bypass channel 120 with the third dielectric layer 706. The microfluidics chip may be aligned with the ports 707 and anodically bonded with the third dielectric layer 706. The microfluidics chip may be made by etching patterns into a borosilicate wafer. Borosilicate may be composed of about 80% silica, about 13% boric oxide, about 3% aluminum oxide, and about 4% sodium oxide. Microfluidic channels can have a depth of 2-3 µm. Ports such as inlet 125 and outlet 135 and, if necessary, electrical connections maybe ultrasonically drilled into the borosilicate wafer. Anodical bonding supports a high-pressure (<300 psi) driven fluidic system. A high voltage (>1000 V) and bonding time (>30 minutes) may be utilized. The borosilicate wafer not only can carry a microfluidic network, but also can function as a handling wafer for subsequent bonding with the electric circuit 150. FIG. 15A and FIG. 15B show a top view image of a microfluidic network and its overlay with the nanogap device.

FIGS. 14A-14D show an exemplary process for connecting the electrode pairs 110 to the electric circuit 150.

Figure 14A:
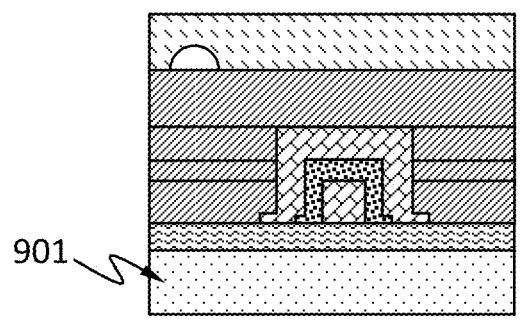
FIGS. 14A-14D show an exemplary process for connecting the electrode pairs to the electric circuit, according to an embodiment.

As shown in FIG. 14A, a device fabricated by the process in FIGS. 9A-9D is obtained, either before or after the sacrificial layer 904 is removed. The process in FIGS. 14A-14D also applies to a device fabricated by the process in FIG. 6A-6F, 7A-7D or 11A-11E.

Figure 14B:
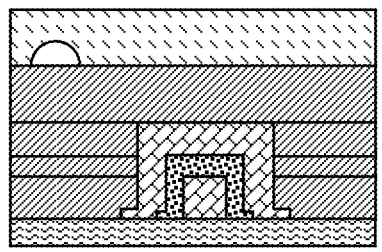

As shown in FIG. 14B, the substrate 901 is removed by a suitable method such as silicon etching, to expose the layer 902 of insulator.

Figure 14C:
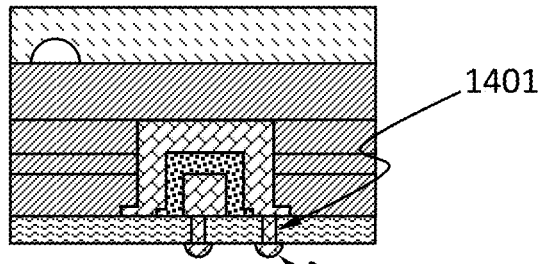

As shown in FIG. 14C, vias 1401 and microbumps 1402 are fabricated in and on the layer 702 of insulator to electrically connect the electrode pairs 110.

Figure 14D:
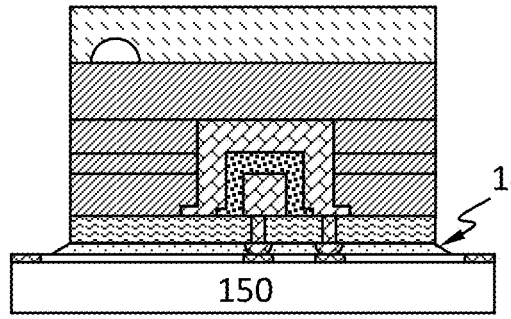

As shown in FIG. 14D, the electric circuit 150 is bonding to the electrode pairs through the vias 1401 and the microbumps 1402, and an underfill 1403 may be disposed to fill void among the microbumps 1402.

EXAMPLES

Disclosed herein is a method comprising: depositing a second electrode of each of a plurality of electrode pairs onto a substrate, through an opening of one or more resist layers; depositing a strip of a sacrificial layer directly on the second electrode through the same opening of the one or more resist layer; depositing a first electrode of each of the plurality of electrode pairs directly on the strip of the sacrificial layer through the same opening of the one or more resist layer; and forming a nanogap channel by removing the strip of the sacrificial layer; wherein the strip of the sacrificial layer is sandwiched between and in direct contact with the first electrode and the second electrode before the strip is removed, and wherein at least a portion of the first electrode directly faces at least a portion of the second electrode.

Disclosed herein is a method comprising: depositing a first electrode and a second electrode of each of a plurality of electrode pairs, through a same opening formed in a resist layer by a single lithography process; wherein the first electrode and the second electrode are separated by a nanogap channel; wherein at least a portion of first electrode directly faces at least a portion of the second electrode; and wherein the at least portion of first electrode and the at least portion of second electrode are exposed to an interior of the nanogap channel.

According to an embodiment, the second electrode is deposited using a directional deposition technique.

According to an embodiment, the directional deposition technique is thermal evaporation or e-beam evaporation.

According to an embodiment, the strip of the sacrificial layer is deposited using a non-directional technique.

According to an embodiment, the non-directional deposition technique is sputtering.

According to an embodiment, the first electrode is deposited using a non-directional deposition technique.

According to an embodiment, the non-directional deposition technique is sputtering.

According to an embodiment, the first electrode is deposited using a directional deposition technique.

According to an embodiment, the non-directional deposition technique is sputtering.

According to an embodiment, the methods further comprise enlarging the opening.

According to an embodiment, the opening is enlarged before the strip of the sacrificial layer is deposited.

According to an embodiment, the opening is enlarged by oxygen plasma etching.

According to an embodiment, the first electrode and the second electrode are not electrically shorted.

According to an embodiment, the at least portion of first electrode and the at least portion of second electrode are exposed to an interior of the nanogap channel.

According to an embodiment, the nanogap channel has a height of 100 nm or less, 75 nm or less, 50 nm or less, 25 nm or less, 10 nm or less, 5 nm or less, or 1 nm or less.

According to an embodiment, the first electrode and the second electrode comprise one or more materials selected from a group consisting of gold, platinum, palladium, silver, boron doped diamond, and, alloys, mixtures and composites thereof.

According to an embodiment, the first electrode and the second electrode do not dissolve in water.

According to an embodiment, the nanogap channel fluidically and sequentially extends across each of the plurality of electrode pairs.

According to an embodiment, the nanogap channel has a width of 500 nm or less, 250 nm or less, 100 nm or less, 50 nm or less, or 10 nm or less.

According to an embodiment, the nanogap channel has a cross-sectional shape of rectangular, square, circular, elliptical shape.

According to an embodiment, the first and second electrodes are configured to be electrically biased.

According to an embodiment, the plurality of electrode pairs consist of two electrode pairs.

According to an embodiment, the plurality of electrode pairs consist of three electrode pairs.

According to an embodiment, the plurality of electrode pairs are configured to identify products of incorporation reactions of nucleotides into a complementary strand to a DNA molecule being sequenced.

According to an embodiment, the plurality of electrode pairs are configured to identify products of digestion of a DNA molecule being sequenced.

According to an embodiment, the methods further comprise patterning a bioreactor.

According to an embodiment, the bioreactor is arranged such that all reaction products from the bioreactor flow into the nanogap channel and by the plurality of electrode pairs.

According to an embodiment, the bioreactor is inside the nanogap channel.

According to an embodiment, the bioreactor is an area with a functionalized surface.

According to an embodiment, a molecule is immobilized to the bioreactor, wherein the molecule is selected from a group consisting of a polymerase, a nuclease, a DNA or RNA strand, and a peptide.

According to an embodiment, the methods further comprise bonding a microfluidics chip comprising a bypass channel.

According to an embodiment, the bypass channel is fluidically parallel with the nanogap channel.

According to an embodiment, the strip of the sacrificial layer is removed by etching.

According to an embodiment, the methods further comprise bonding an electric circuit to the plurality of electrode pairs through vias and microbumps.

According to an embodiment, a portion of the nanogap channel sandwiched between the at least portion of the first electrode and the at least portion of the second electrode has a length to width ratio of greater than 50:1, greater than 100:1, greater than 500:1, greater than 1000:1, or greater than 2000:1.

The descriptions above are intended to be illustrative, not limiting. Thus, it will be apparent to one skilled in the art that modifications may be made to the embodiments as described without departing from the scope of the claims set out below.

What is claimed is:

1. A method comprising:
   depositing a second electrode of each of a plurality of electrode pairs onto a substrate, through an opening of one or more resist layers;

depositing a strip of a sacrificial layer directly on the second electrode through the same opening of the one or more resist layer;

depositing a first electrode of each of the plurality of electrode pairs directly on the strip of the sacrificial layer through the same opening of the one or more resist layer; and forming a nanogap channel by removing the strip of the sacrificial layer;

wherein the strip of the sacrificial layer is sandwiched between and in direct contact with the first electrode and the second electrode before the strip is removed, and wherein at least a portion of the first electrode directly faces at least a portion of the second electrode, further comprising enlarging the opening by enlarging the one or more resist layers after the depositing the second electrode and prior to the depositing the first electrode.

2. The method of claim 1, wherein the second electrode is deposited using a directional deposition technique.

3. The method of claim 1, wherein the strip of the sacrificial layer is deposited using a non-directional technique.

4. The method of claim 1, wherein the first electrode is deposited using a non-directional deposition technique.

5. The method of claim 1, wherein the first electrode is deposited using a directional deposition technique.

6. The method of claim 1, wherein the opening is enlarged before the strip of the sacrificial layer is deposited.

7. The method of claim 1, wherein the opening is enlarged by oxygen plasma etching.

8. The method of claim 1, wherein the first electrode and the second electrode are not electrically shorted.

9. The method of claim 1, wherein the at least portion of first electrode and the at least portion of second electrode are exposed to an interior of the nanogap channel.

10. The method of claim 1, wherein the nanogap channel has a height of 100 nm or less, 75 nm or less, 50 nm or less, 25 nm or less, 10 nm or less, 5 nm or less, or 1 nm or less.

11. The method of claim 1, further comprising bonding a microfluidics chip comprising a bypass channel fluidically parallel with the nanogap channel.

12. The method of claim 1, wherein a portion of the nanogap channel sandwiched between the at least portion of the first electrode and the at least portion of the second electrode has a length to width ratio of greater than 50:1, greater than 100:1, greater than 500:1, greater than 1000:1, or greater than 2000:1.

13. The method of claim 1, wherein the nanogap channel fluidically and sequentially extends across each of the plurality of electrode pairs.

14. The method of claim 13, wherein the bioreactor is an area with a functionalized surface.

15. The method of claim 1, further comprising patterning a bioreactor.

16. The method of claim 15, wherein the bioreactor is arranged such that all reaction products from the bioreactor flow into the nanogap channel and by the plurality of electrode pairs.

17. The method of claim 15, wherein the bioreactor is inside the nanogap channel.

18. The method of claim 15, wherein a molecule is immobilized to the bioreactor, wherein the molecule is selected from a group consisting of a polymerase, a nuclease, a DNA or RNA strand, and a peptide.

* * * * *